United States Patent
Assmann

(10) Patent No.: US 8,077,941 B2
(45) Date of Patent: Dec. 13, 2011

(54) METHOD AND IMAGING PROCESSING UNIT AND MEDICAL IMAGING DEVICE FOR PRODUCING A CONTRAST ENHANCED IMAGE DATA RECORD OF AN EXAMINATION REGION OF A PATIENT

(75) Inventor: Stefan Assmann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1112 days.

(21) Appl. No.: 11/902,582

(22) Filed: Sep. 24, 2007

(65) Prior Publication Data

US 2008/0091100 A1 Apr. 17, 2008

(30) Foreign Application Priority Data

Sep. 25, 2006 (DE) .................. 10 2006 045 174

(51) Int. Cl.
*G06K 9/00* (2006.01)
(52) U.S. Cl. .................. 382/128; 382/130; 382/132
(58) Field of Classification Search ........... 382/128–134
See application file for complete search history.

(56) References Cited

U.S. PATENT DOCUMENTS

| 6,493,569 | B2 * | 12/2002 | Foo et al. .................. 600/410 |
| 2004/0193040 | A1 | 9/2004 | Brill et al. | |

FOREIGN PATENT DOCUMENTS

| DE | 10214254 A1 | 10/2003 |
| DE | 10259793 A1 | 7/2004 |
| EP | 0 994 352 A2 | 4/2000 |
| EP | 0994352 A2 | 4/2000 |
| WO | WO 03/083778 | 10/2003 |

OTHER PUBLICATIONS

Peter Kellman, Yiu-Cho Chung, Orlando P. Simonetti, Elliot R. McVeigh and Andrew E. Arai; Multicontrast Delayed Enhancement Provides Improved Contrast Between Myocardial Infarction and Blood Pool Kellman et al.; Journal of Magnetic Resonance Imaging 22:605-613 (2005); Others; 2005.
201. Multi-contrast Delayed Enhancement Imaging for Improved Detection of Subendocardial Infarcts Oral Abstract / Jcariovac MR, vol. 7 (1) 2005, Seiten 84 und 85; Oral Abstract / Jcariovac MR, vol. 7 (1) 2005, Seiten 84 und 85; Others; 2005.

(Continued)

*Primary Examiner* — Wesley Tucker
(74) *Attorney, Agent, or Firm* — Harness, Dickey & Pierce, P.L.C.

(57) ABSTRACT

In order to produce a contrast enhanced image data record of an examination region of a patient, a method is disclosed. In at least one embodiment, the method includes loading a first image data record of the examination region in the case of which healthy tissue is displayed with a lower intensity than blood and diseased tissue, and a second image data record of the examination region in the case of which blood is displayed with a lower intensity than healthy and diseased tissue. In at least one embodiment, the contrast enhanced image data record is produced by processing the first image data record and the second one, the processing including at least one arithmetic operation, and is thereupon displayed and/or stored. In further embodiments are provided a computer readable medium including a program that implements at least one embodiment of such a method on an arithmetic logic unit, an imaging processing unit that is designed for carrying out a method according to at least one embodiment, and a medical imaging device, in particular an MR device, having an image processing unit that is designed to carry out a method according to at least one embodiment of the invention.

15 Claims, 4 Drawing Sheets

OTHER PUBLICATIONS

Helbig, Christian: Zeitaufgelöste MR-Angiographie der Nierenarterien—Morphologie und Perfusion; Inaugural-Dissertation, Würzburg, Mai 2006; S. 13-19; Others; 2006; DE (Original and English translation).

Multicontrast Delayed Enhancement Provides Improved Contrast Between Myocardial Infyrction and Blood Pool; Kellman P. et al, Journal of Magnetic Resonance Imaging 22: 605-613 (2005).

Multi-Contrast Delayed Enhancement Imaging for Improved Detection of Subendocardial Infarcts; Kellman P. et al; Oral Abstracts, 84-85.

German Office Action.

Helbig, Christian: Zeitaufgelöste MR-Angiographie der Nierenarterien—Morphologie und Perfusion; Inaugural-Dissertation, Würzburg, Mai 2006; S. 13-19; Others; 2006; DE.

* cited by examiner

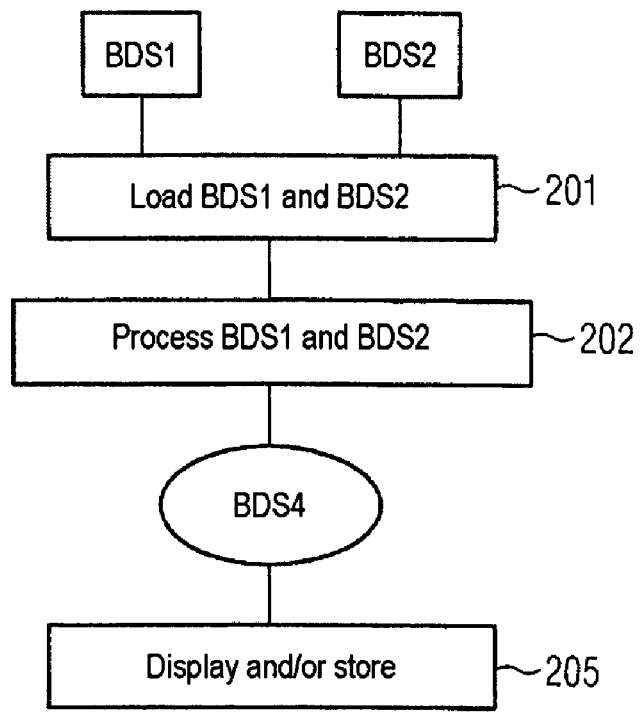
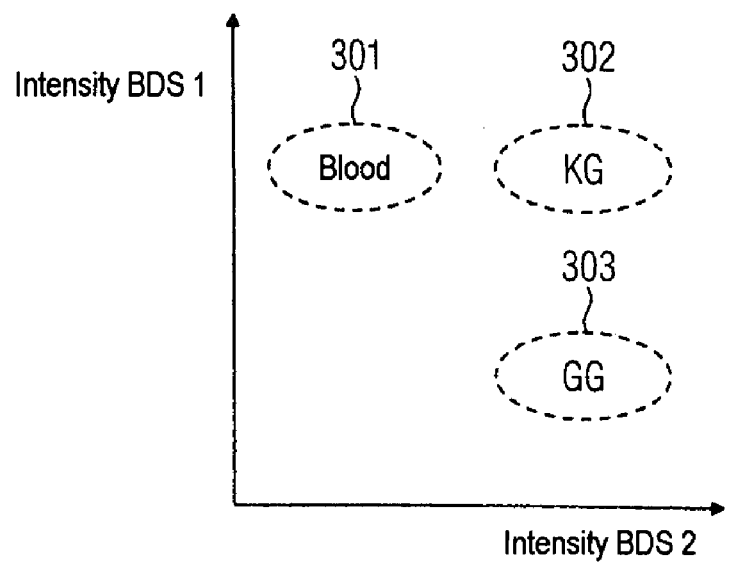

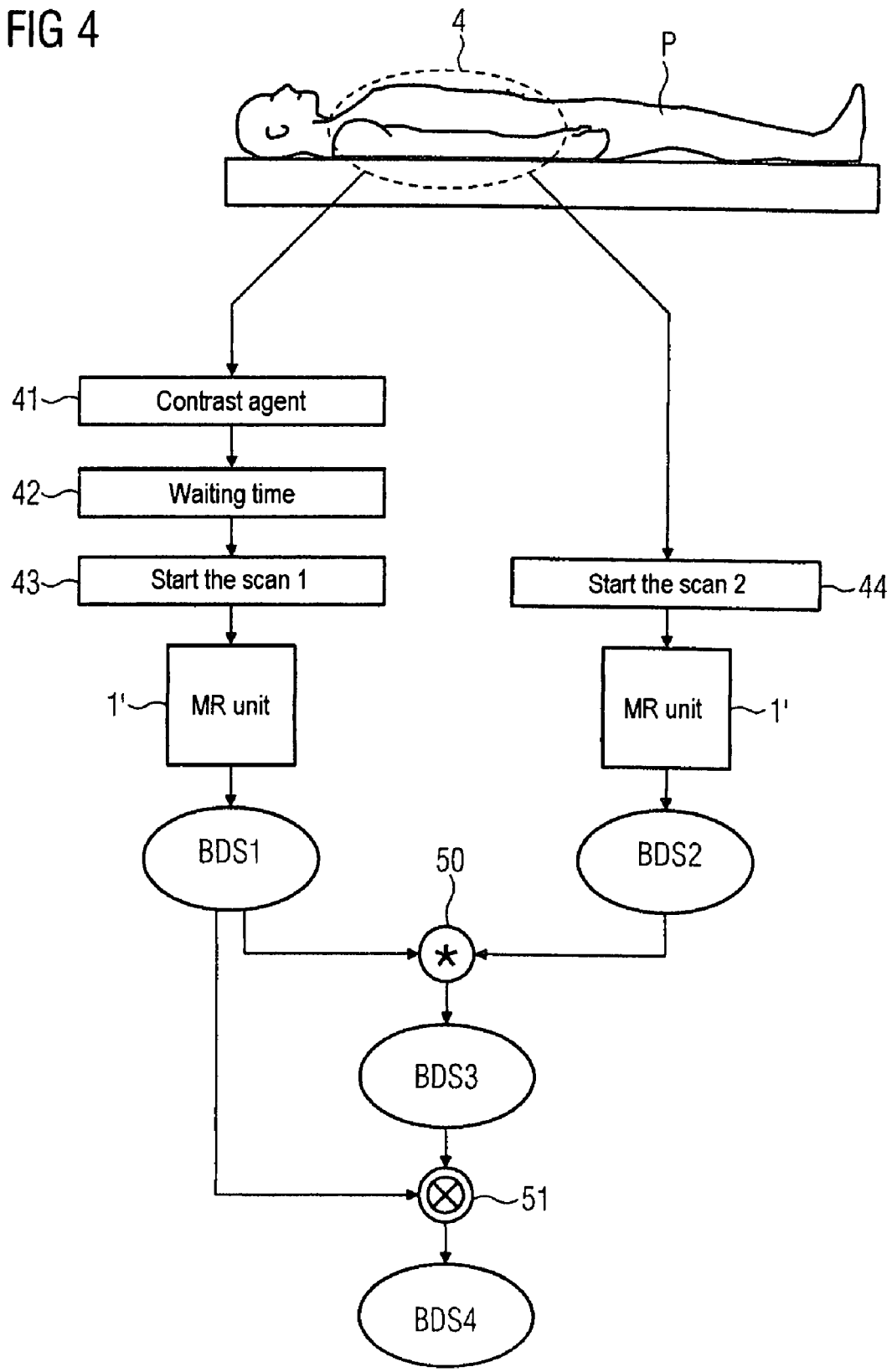

US 8,077,941 B2

METHOD AND IMAGING PROCESSING UNIT AND MEDICAL IMAGING DEVICE FOR PRODUCING A CONTRAST ENHANCED IMAGE DATA RECORD OF AN EXAMINATION REGION OF A PATIENT

PRIORITY STATEMENT

The present application hereby claims priority under 35 U.S.C. §119 on German patent application number DE 10 2006 045 174.0 filed Sep. 25, 2006, the entire contents of which is hereby incorporated herein by reference.

FIELD

Embodiments of the invention generally relate to a method, an image processing unit and/or a medical imaging device, in particular a magnetic resonance device, for producing a contrast enhanced image data record of an examination region of a patient.

BACKGROUND

Modern imaging techniques in medicine such as, for example, computed tomography, ultrasound and magnetic resonance tomography, facilitate for doctors the noninvasive diagnosis relating to an examination region of a patient. The various imaging techniques are suitable with different success for qualitatively high value scans depending on the tissue to be examined. Because of its good soft part contrast, which is well known, the magnetic resonance technique is highly suitable for soft part display. It renders it possible, inter alia, to scan the same tissue with different contrasts, and thus to highlight various regions of the examination zone differently, depending on requirement.

The magnetic resonance technique (the abbreviation MR stands below for magnetic resonance) is a known technique with the aid of which images of the interior of an examination object can be produced. In simple terms, to this end the examination object is positioned in an MR unit in a comparatively strong static, homogeneous basic magnetic field (field strengths of 0.2 tesla to 7 tesla and more) such that the nuclear spins thereof are oriented along the basic magnetic field. To excite nuclear spin resonances, radiofrequency excitation pulses are irradiated into the examination object, the excited nuclear spin resonances are measured, and MR images are reconstructed on the basis of them. Rapidly switched magnetic gradient fields are superposed on the basic magnetic field for local coding of the measured data. The recorded measured data are digitized and stored as complex numerical values in a k space matrix. An associated MR image can be reconstructed from the k space matrix occupied with values by means of a multidimensional Fourier transformation.

A diagnosis frequently requires ability to distinguish healthy tissue from diseased tissue. A specific technique of visualizing diseased—for example acutely necrotic or scarred—tissue is late enhancement or delayed enhancement. In this case, use is made of the fact that in the course of time an administered contrast agent containing gadolinium, magnesium or iron, for example, is enriched later in diseased tissue than in healthy tissue, and this is visualized by means of suitable MR sequences. Healthy areas from which the contrast agent has already been washed away again after a waiting time therefore emit an only weak signal—and therefore appear dark, whereas enriched areas develop strong signals and are therefore displayed bright. The maximum contrast is typically achieved 10 to 15 minutes after administration of contrast agent. This technique therefore offers a good contrast between healthy, nonenriched tissue areas, and diseased, enriched tissue areas.

EP 0 994 352 A2 discloses an application of a late enhancement for examining microcardial. However, the contrast between diseased tissue and healthy tissue is certainly good, depending on the sequences used, but the frequently additionally desired contrast between diseased tissue and blood is generally not sufficient to enable a reliable distinction. For example, in the case of inner layer damage to the heart after a heart attack, this damage can frequently not be delimited from the adjoining blood volume. Again, the dosage of the contrast agent, the waiting time and the washout rate influence the image quality and can complicate a diagnosis.

In order to circumvent the problems named, it is possible to intercompare a number of image data obtained in various ways. A method for simultaneously recording two late enhancements is disclosed in an article by P. Kellman et al. (Multicontrast Delayed Enhancement Provides Improved Contract Between Myocardial Infarction and Blood Pool, Journal of Magnetic Resonance Imaging 22: 605-613, 2005). One scan is recorded with a $T_1$ weighted contrast, the other with a $T_2$ weighted contrast. By comparing the two scans, it is intended here to be able to distinguish infarcated myocardial tissue more effectively from blood. This comparison can be performed, inter alia, by taking the quotient of the two scans. However, in this context difficulties are mentioned with this approach since, instead of a desired increase in the contrast between infarcated myocardial and blood, the exact opposite, a reduction in this contrast, has also been obtained.

SUMMARY

The inventors recognized that there is thus still a need for methods for improving the contrast of medical scans of examination regions.

In at least one embodiment of the invention, a contrast enhanced image data record of an examination region of a patient is enabled to be produced in a way that can be employed with versatility and low outlay.

According to at least one embodiment of the invention, a first image data record of the examination region in the case of which healthy tissue is displayed with lower intensity than diseased tissue and blood, and a second image data record, in the case of which blood is displayed with a lower intensity than healthy tissue and diseased tissue, are leaded. The diseased tissue can be, for example, necrotic or scarred tissue of the heart or another organ or muscle of a patient.

The two data records are processed with low outlay by means of at least one arithmetic operation provided for imaging processing, for example pixel by pixel, to form a contrast enhanced image data record. The contrast enhanced image data record thus produced is displayed and/or stored.

The specified method of at least one embodiment is the more efficient, on the one hand, the lower the intensity in the first image data record with which the healthy tissue is displayed—by comparison with the intensity with which the diseased tissue and blood are represented—and, on the other hand, the lower the intensity in the second image data record with which blood is displayed—by comparison with the intensity with which the diseased tissue and the healthy tissue are displayed. In this case, the difference in intensity between diseased tissue and blood in the first image data record, and the difference in intensity between healthy and diseased tissue in the second image data record are not relevant, in particular they can also be relatively small to zero.

An advantage of at least one embodiment of the method thus results in the fact that there is produced from two different image data records that do not respectively suffice in themselves to ensure via their contrasts a reliable distinction of the three items of blood, healthy tissue and diseased tissue, a contrast enhanced image data record that permits this distinction to be made. Since the diseased tissue is displayed brightly both in the first and in the second image data record, regions relating to this diseased tissue, in particular, can be identified easily purely by applying simple image processing measures.

It is usual for the first and second image data records to be recorded roughly at the same time and/or under the same conditions. It is thereby possible, inter alia, respectively to compare directly the shape, position and size of the imaged examination region, for example without prior recording, and this favors the method. In the case of scans of the heart, this can be achieved, for example, by virtue of the fact that the two image data records are respectively acquired at the same instant within the cardiac cycle and respiratory cycle.

The first image data record is preferably recorded after administration of a contrast agent and waiting for a suitable waiting time, typically 10 to 30 minutes. In this way, the intensity of diseased tissue is increased against that of healthy tissue in the scan.

In the case of the method according to at least one embodiment of the invention, it is advantageous to use an MR unit for recording at least one of the image data records. MR tomography offers particularly variable—and thus advantageous—possibilities of settings for the imaging of soft parts, in particular as regards the soft part contrast, and can therefore be used in a versatile fashion. An MR unit usually has a multiplicity of sequences that can be used to record image data records with contrasts such as are provided for the first or second image data record.

In a particularly advantageous way, the first image data record is recorded approximately 10 to 30 minutes after administration of a contrast agent, this being done by means of a late enhancement with $T_1$ weighted contrast, for example by way of an Inversion Recovery TrueFISP sequence. Such a scanning technique can be carried out without a high outlay, and produces a first image data record in the case of which healthy tissue is displayed with a lower intensity than blood and diseased tissue, and so the healthy tissue can easily be identified by a user.

In order to record the second image data record, in the case of which blood is displayed with preferably conspicuously lower intensity than healthy and diseased tissue, it is expedient to suppress the signal of the blood. This can be achieved by specific MR sequences. Since the blood then mostly appears black, such a scan is also denoted as a dark blood scan or black blood scan. In the case of flowing blood, it is therefore theoretically sufficient to select the echotime (TE) to be long enough that the blood continues to flow between a pulse and its echo, and thus loses its signal. Nowadays, the dark blood effect is often artificially brought about, thus shortening the scanning times. Current suitable sequences are, for example, DIR $T_1$ (double inversion recovery $T_1$) or dual inversion technique. In the case of the dual inversion technique, a first inversion pulse dephases the blood in such a way that the signals of the spins cancel one another out and it is therefore impossible to measure any further signal from the blood. A second inversion pulse rephases the tissue, which therefore supplies a normal signal. A normal contrast in the tissue is therefore obtained, whereas the blood appears dark.

It is particularly advantageous to use a $T_1$ weighted scanning sequence that operates with one of the abovedescribed techniques.

When processing the first and the second image data records in order to produce the contrast enhanced image data record, it is preferred to apply at least one arithmetic operation in the form of a, for example pixel by pixel, multiplication and/or addition in order to process the images of the two loaded image data records with a low outlay. One advantage of an addition is that it is impossible to encounter undefined results such as, for example, in the case of a division by zero.

In a further refinement of at least one embodiment of the invention, the first and the second image data records are firstly processed by means of an arithmetic operation, for example pixelwise multiplication, and a mask is produced on the basis thereof. By way of example, to this end all regions that undershoot or overshoot a prescribed limiting value are masked out and/or marked in the display. The mask is then laid over an image data record of the examination region, for example the original first or second image data record. Such a mask can also be applied to later scans, for example as an aid for—automatically—determining possible changes in the extent of the diseased tissue.

It is particularly expedient to use at least one embodiment of an inventive production of a contrast enhanced image data record for examining a patient's heart after a heart attack, for example. Infarcated, scarred or wounded tissue of the cardiac muscle is often situated at the inner wall of the heart, and therefore near the ventricle filled with blood, and this has so far rendered it difficult to find the areas of diseased tissue.

Furthermore, a computer program is provided that implements at least one embodiment of an inventive method on an arithmetic logic unit when it is executed on the arithmetic logic unit, and so are an image processing unit that is designed for carrying out at least one embodiment of the inventive method, as well as a medical imaging device, in particular an MR unit, with an image processing unit that is designed for carrying out at least one embodiment of the inventive method.

At least one embodiment of the inventive imaging device has the advantage that it can be used to record the image data records from which the contrast enhanced image data record can be produced in a second step. This provides a user with a single unit with which he can carry out all the steps of imaging up to the production of the contrast enhanced image.

BRIEF DESCRIPTION OF THE DRAWINGS

Example embodiments of the invention with refinements will be explained hereafter. Examples set forth do not constitute a restriction of the invention. In particular, the size ratios are purely schematic. In the drawings:

FIG. 2 shows a flowchart of an embodiment of the method for producing a contrast enhanced image data record of an examination region of a patient, FIG. 3 shows a schematic illustration of the intensity distribution of the three items of blood, healthy and diseased tissue in the first and second image data records, FIG. 4 shows a flowchart of an embodiment of preferred production of a contrast enhanced image data record.

DETAILED DESCRIPTION OF THE EXAMPLE EMBODIMENTS

Figure 1:
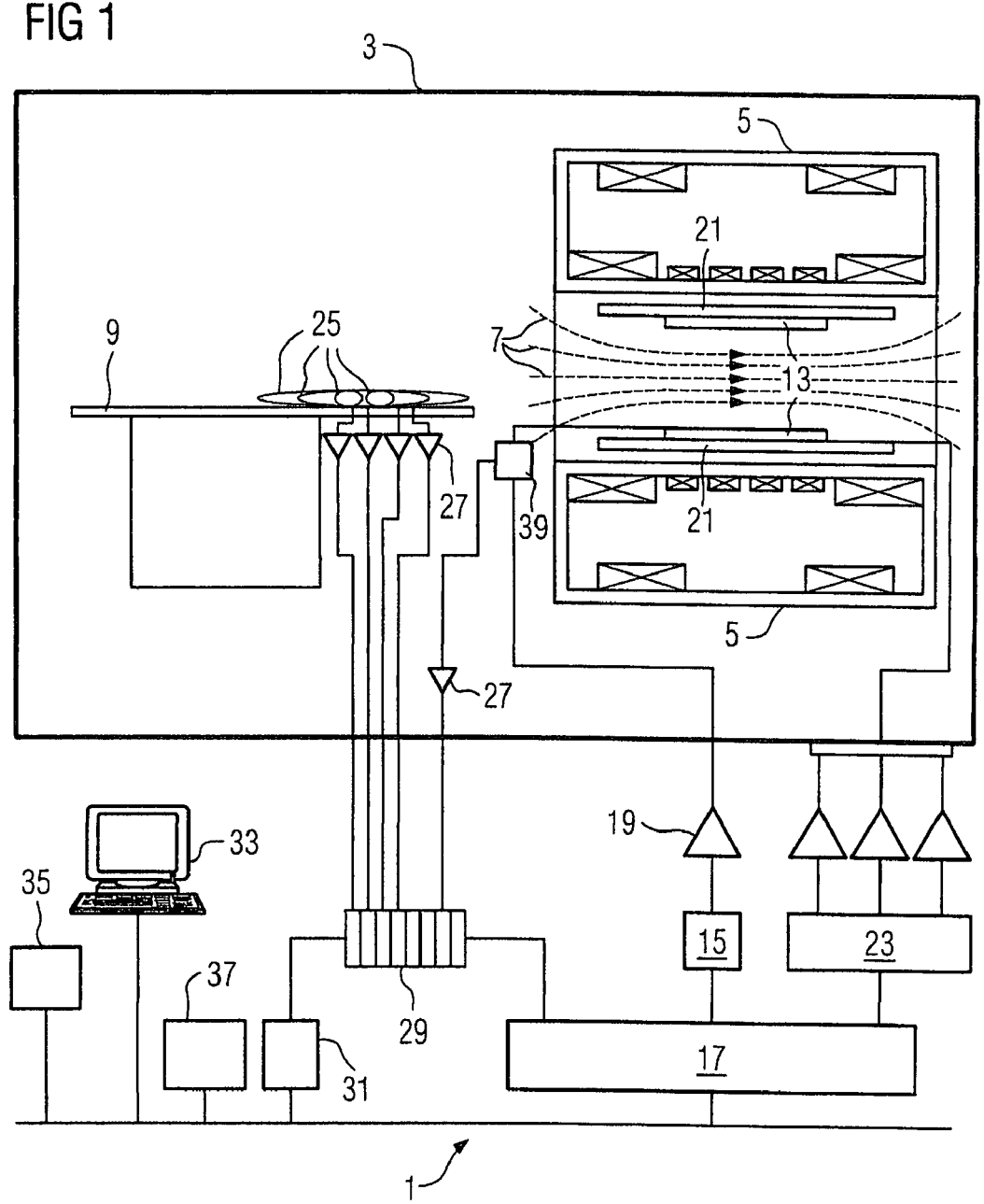
FIG. 1 shows a schematic design of a magnetic resonance unit.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows a schematic design of a magnetic resonance unit 1 with its essential components. In order to examine a body by means of magnetic resonance imaging, various magnetic fields that are tuned to one another very exactly in terms of their temporal and spatial characteristics are irradiated onto the body.

A strong magnet, usually a cryomagnet 5 with a tunnel-shaped opening, arranged in a measurement cabin 3 screened against radiofrequency produces a static strong main magnetic field 7 that is usually 0.2 tesla to 3 tesla and more. A body or a body part—not illustrated here—to be examined is supported on a patient couch 9 and positioned in the homogeneous region of the main magnetic field 7.

The excitation of the nuclear spins of the body is performed via magnetic radiofrequency excitation pulses that are irradiated via a radiofrequency antenna illustrated here as a body coil 13. The radiofrequency excitation pulses are generated by a pulse generating unit 15 that is controlled by a pulse sequence control unit 17. After being amplified by a radiofrequency amplifier 19, they are conducted to the radiofrequency antenna. The radiofrequency system shown here is indicated merely schematically. It is customary to use more than one pulse generating unit 15, more than one radiofrequency amplifier 19 and a number of radiofrequency antennas in a magnetic resonance unit 1.

The magnetic resonance unit 1 further has gradient coils 21 that are used during a measurement to irradiate magnetic gradient fields for selective slice excitation and for local coding of the measurement signal. The gradient coils 21 are controlled by a gradient coil control unit 23 that, just like the pulse generating unit 15, is connected to the pulse sequence control unit 17.

The signals emitted by the excited nuclear spins are received by the body coil 13 and/or by local coils 25, amplified by assigned radiofrequency amplifiers 27, and further processed and digitized by a receiving unit 29.

In the case of a coil that can be operated both in transmit and in receive mode, such as, for example, the body coil 13, the correct signal relaying is controlled by an upstream duplexer 39.

An image processing unit 31 produces from the measured data an image that is displayed to a user via an operator console 33 or stored in a memory unit 35. A central arithmetic logic unit 37 controls the individual system components, particularly during the recording of the measured data. The image processing unit 31 and/or the arithmetic logic unit 37 are designed in this case such that they can be used to carry out at least one embodiment of the inventive method. By way of example, to this end an inventive computer program is installed such that it can executed on the arithmetic logic unit 37 and/or image processing unit 31.

However, an image processing unit 31 that is designed for carrying out an embodiment of the inventive method can also be operated independently of a magnetic resonance unit 1.

FIG. 2 is a schematic of the cycle of an embodiment of a method for producing a contrast enhanced image data record of an examination region of a patient from a first image data record (also denoted as BDS1 in the figures), this data record having a lower intensity in regions in which healthy tissue is displayed than in regions in which diseased tissue and/or blood are displayed, and a second image data record (also denoted as BDS2 in the figures) that, by contrast, has a lower intensity in regions in which blood is displayed than in regions in which healthy and/or diseased tissue are displayed. A schematic of a preferred intensity distribution of the three items of blood, healthy tissue and diseased tissue in the two image data records is illustrated in FIG. 3. In a first step 201, the two image data records of the examination region are loaded with different contrast values and/or intensity distributions.

In a second step 202, the first image data record BDS1 and the second image data record BDS2 are processed by way of at least one arithmetic operation in order to obtain a contrast enhanced image data record (also denoted as BDS4 in the figures), of which the contrast values are enhanced in such a way that it is possible to distinguish both healthy tissue from diseased tissue, and healthy tissue from blood as well as diseased tissue from blood, such that the abovenamed three items (blood, healthy tissue, diseased tissue) can be uniquely identified for a user with the aid of this contrast enhanced image data record. The contrast enhanced image data record BDS4 is displayed in a third step 205, and/or stored for later use. An example processing of the first image data record BDS1 with the second image data record BDS2 to form a contrast enhanced image data record BDS4 will be described later in FIG. 4.

FIG. 3 shows a schematic of a preferred intensity distribution in the first and second image data records. In the first image data record BDS1, the intensity distribution of the blood 301 illustrated is approximately at the same level as the intensity distribution of the illustrated diseased tissue (denoted as KG in FIG. 3) 302. By contrast, the intensity distribution of the imaged healthy tissue (denoted as GG in FIG. 3) 303 is situated much lower, and can therefore easily be identified on a scan of the first image data record BDS1. In turn, the result of the second image data record BDS2 is an approximately uniformly distributed intensity distribution for the imaged healthy tissue 303 and the imaged diseased tissue 302, but the intensity distribution of the displayed blood 301 is situated far below these two values, for which reason blood can easily be recognized in this second image data record BDS2. It can clearly be seen in this two dimensional illustration how, in the two illustrated image data records, the intensities, which correspond to gray scale values, respectively form clusters for each of the three items (blood, healthy and diseased tissue) of which in each case two can differ only by the two dimensional illustration both in the first and in the second image data record. This fact is utilized in order to produce a contrast enhanced image data record that allows the three said items to be distinguished in one dimension (gray scale values in a scan) as well.

FIG. 4 illustrates the cycle of a preferred production of a contrast enhanced image data record. The examination region U of a patient P is recorded in this example in at least two image data records respectively having different contrasts, by means of an MR unit 1'.

A contrast agent 41 is administered to the patient P in order to record a first image data record BDS1. After a prescribed waiting time 42 has been waited, the recording 43 of the first image data record is started. Using suitable sequences, for example an Inversion Recovery TrueFISP sequence, an MR unit 1' produces the first image data record BDS1, in which healthy tissue is displayed with a lower intensity than diseased tissue and blood. The contrast relationships of an exemplary first image data record BDS1 are illustrated schematically in FIG. 5.

In the example shown, a further scan 44 of the examination region is started, expediently with an identical image section, and produces by suitable sequence selection, for example a so-called dark blood scan with $T_1$ weighted contrast, a second image data record BDS2 in which blood is displayed with a lower intensity than healthy and diseased tissue. The contrast relationships of an exemplary second image data record BDS2 are illustrated schematically in FIG. 6.

The first and the second image data records BDS1 and BDS2 are processed with one another by an image processing measure 50—illustrated in this example by multiplication, by way of example. The result of this multiplication is a first contrast enhanced image data record BDS3 in which the diseased tissue has a higher intensity than the healthy tissue and blood, and which therefore enables a user at least to identify the diseased tissue, if it is not always possible to distinguish all three items of blood, healthy and diseased tissues. The contrast relationships of an exemplary first contrast enhanced image data record BDS3 are illustrated schematically in FIG. 7.

If it is desired to have a further enhancement of the contrast of the first enhanced image data record BDS3, the first contrast enhanced image data record BDS3 can be further processed once again by means of a further image processing measure 51 with one of the two first image data records, in the example with the first image data record. An addition is an obvious choice as further image processing measure 51. The second contrast enhanced image data record BDS4 thus produced exhibits different intensities for the three different items of blood, healthy and diseased tissue. In the example of an addition of the first image data record BDS1 with the first contrast enhanced image data record BDS3 as further image processing measure 51, the second contrast enhanced image data record BDS4 exhibits a lower intensity for healthy tissue than for blood, the intensity of the blood being, in turn, lower than the intensity of the diseased tissue. It is thereby possible for all three items named to be effectively distinguished from one another. The contrast conditions of an exemplary second contrast enhanced image data record BDS4 are illustrated schematically in FIG. 8.

Instead of an addition as further image processing measure 51, it is also possible for a mask produced on the basis of the first contrast enhanced image data record BDS3 to be, for example, superposed on the first image data record BDS1 in order thus to obtain a second contrast enhanced image data record BDS4.

The same imaging device need not necessarily be used for the recording of the first and the second image data records. It is also conceivable to carry out the two recordings with the aid of different imaging devices that can, in particular, also make use of different imaging techniques. In such a case, the method can be favored by mutually registering the two image data records before the further processing.

FIGS. 5 to 8 illustrate schematically the contrast conditions in various image data records BDS1, BDS2, BDS3 and BDS4 with the aid of a short axis section that shows the cardiac muscle 63, 65 and the interior of the heart, filled with blood 64. The cardiac muscle can be subdivided into healthy tissue 63 and diseased tissue 65, for example infarcated myocardial tissue. The dashed rims of the various regions serve the purpose of an orientation. They are not to be seen on real image data records.

Figure 5:
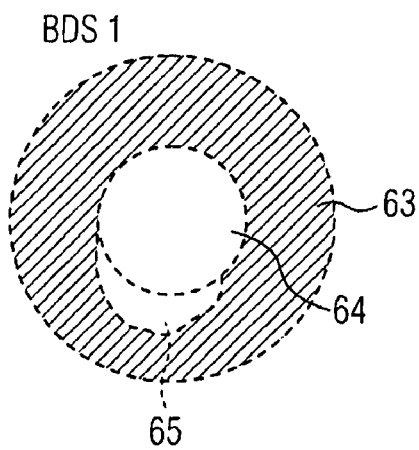
FIG. 5 shows a schematic illustration of the contrast relationships in the first image data record with the aid of a short axis section of the heart.

FIG. 5 shows schematically the contrast relationships of a scan of a first image data record BDS1 of an examination region with the aid of a short axis section of the heart. The intensity with which the diseased tissue 65 is displayed is of the same order of magnitude as the intensity with which the blood 64 is displayed. Consequently, it is possible to distinguish between these two regions only poorly. The intensity with which the healthy tissue 63 is displayed is, however, substantially lower than the intensities previously mentioned. Consequently, the region of the healthy tissue 63 can be effectively distinguished in the first image data record BDS1 from the blood 64 and the diseased tissue 65.

Figure 6:
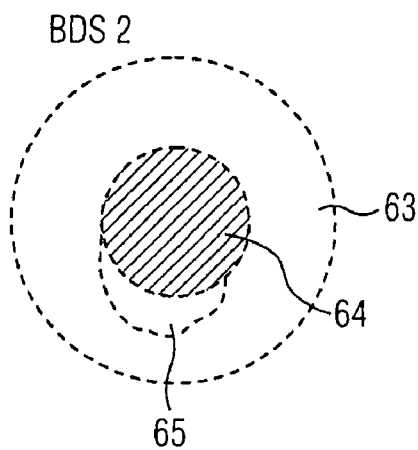
FIG. 6 shows an analogous schematic illustration of the contrast relationships in the second image data record.

By analogy with FIG. 5, FIG. 6 illustrates schematically a scan of a second image data record BDS2 of the examination region. It is possible here to distinguish only poorly between the various regions of the cardiac muscle, since the intensity with which the healthy tissue 63 is displayed is of the same order of magnitude as the intensity with which the diseased tissue 65 is displayed. In exchange, the intensity with which the blood 64 is displayed is here substantially lower than the intensities previously mentioned. Consequently, the region of the blood 64 can be effectively distinguished in the second image data record BDS2 from the healthy tissue 63 and the diseased tissue 65.

Figure 7:
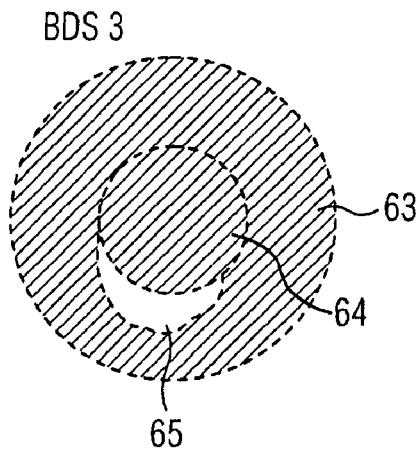
FIG. 7 shows a schematic illustration of the contrast relationships of a first contrast enhanced image data record produced by means of multiplication of the first image data record by the second one.

FIG. 7 shows schematically a first contrast enhanced image data record BDS3 that has been produced by multiplying the first image data record BDS1 by the second image data record BDS2. As an example of the multiplication, it is now possible for regions that display diseased tissue 65 to be easily identified, since they have a substantially higher intensity than regions of the blood 64 and the healthy tissue 63. Depending on the fundamental contrast of the first image data record BDS1 and the second image data record BDS2, it is already possible here to distinguish all three regions mentioned from one another. In the example shown, the intensities of the two darker regions are of the same order of magnitude. However, it is possible at least to distinguish the bright region of the diseased tissue 65 effectively from the blood 64 and the healthy tissue 63, and this frequently already incorporated information desired by a user. A further enhancement of the contrast can be attained by further processing.

Figure 8:
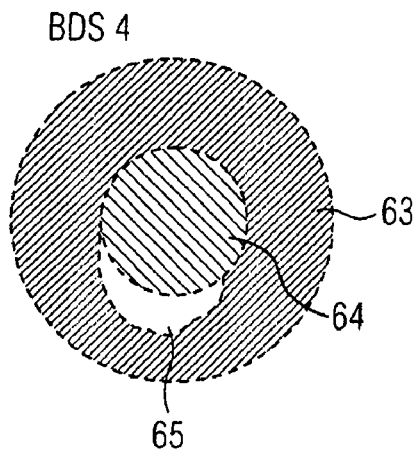
FIG. 8 shows a schematic illustration of the contrast relationships of a second contrast enhanced image data record further processed by way of addition.

FIG. 8 illustrates schematically a second contrast enhanced image data record BDS4 that has been produced by adding the first image data record BDS1 to the first contrast enhanced image data record BDS3. It is now possible here to distinguish all three items of blood 64, healthy tissue 63 and diseased tissue 65 from one another, since they all have easily distinguishable intensities. In this example, the healthy tissue 63 shows the lowest intensity here. The next higher intensity is exhibited by regions of the blood 64, and diseased tissue 65 is displayed most brightly that is to say with the highest intensity.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing a contrast enhanced image data record of an examination region of a patient, comprising:
    loading a first image data record of the examination region in the case of which healthy tissue is displayed with a lower intensity than blood and diseased tissue;
    loading a second image data record of the examination region in the case of which blood is displayed with a lower intensity than healthy tissue and diseased tissue;
    combining the first image data record with the second image data record to produce a contrast enhanced image data record, the combining including at least one arithmetic operation; and
    at least one of displaying and storing the contrast enhanced image data record.

2. The method as claimed in claim 1, wherein at least one of the first and of the second image data records is an image data record of a scan after administration of a contrast agent.

3. The method as claimed in claim 2, wherein at least one of the first and of the second image data records is an image data record of a magnetic resonance tomography scan.

4. The method as claimed in claim 1, wherein the first image data record is an image data record of a late enhancement with weighted contrast.

5. The method as claimed in claim 1, wherein the second image data record is an image data record of a scan with weighted contrast in the case of which the signal of the blood was suppressed.

6. The method as claimed in claim 1, wherein at least one of multiplication and addition is used in the arithmetic operation.

7. The method as claimed in claim 1, wherein the combining of the first image data record with the second one by way of at least one arithmetic operation includes, in a first step, the formation of a mask that is laid in a second step over the first or second image data record.

8. The method as claimed in claim 1, wherein the examination region is the heart, and the diseased tissue is infarcated myocardial tissue.

9. A non-transitory computer readable medium including program segments to, when executed on an arithmetic logic unit, perform:
    loading a first image data record of the examination region in the case of which healthy tissue is displayed with a lower intensity than blood and diseased tissue;
    loading a second image data record of the examination region in the case of which blood is displayed with a lower intensity than healthy tissue and diseased tissue;
    combining the first image data record with the second image data record to produce a contrast enhanced image data record, the combining including at least one arithmetic operation; and
    at least one of displaying and storing the contrast enhanced image data record.

10. An imaging processing unit, comprising:
    means for loading a first image data record of the examination region in the case of which healthy tissue is displayed with a lower intensity than blood and diseased tissue;
    means for loading a second image data record of the examination region in the case of which blood is displayed with a lower intensity than healthy tissue and diseased tissue;
    means for producing a contrast enhanced image data record by combining the first image data record with the second image data record, the combining including at least one arithmetic operation; and
    means for at least one of displaying and storing the contrast enhanced image data record.

11. A medical imaging device, comprising an image processing unit as claimed in claim 10.

12. The medical imaging device of claim 11, wherein the medical imaging device is an MR device.

13. The method as claimed in claim 1, wherein the at least one arithmetic operation is multiplication.

14. The method as claimed in claim 9, wherein the at least one arithmetic operation is multiplication.

15. The method as claimed in claim 10, wherein the at least one arithmetic operation is multiplication.

* * * * *